(12) United States Patent
Wong et al.

(10) Patent No.: US 11,458,575 B2
(45) Date of Patent: Oct. 4, 2022

(54) DEVICE AND METHOD FOR THE PREPARATION AND OPERATION ON BIOLOGICAL SPECIMEN

(71) Applicant: THE REGENTS OF THE UNIVERSITY OF CALIFORNIA, Oakland, CA (US)

(72) Inventors: Brian Jet-Fei Wong, Irvine, CA (US); Guillermo Aguilar, Corona, CA (US); Dmitry Protsenko, Vallejo, CA (US); Lars Svaasand, Trondheim (NO); Cara Chlebicki, Redondo Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 416 days.

(21) Appl. No.: 16/431,055

(22) Filed: Jun. 4, 2019

(65) Prior Publication Data
US 2019/0366485 A1 Dec. 5, 2019

Related U.S. Application Data

(60) Provisional application No. 62/681,079, filed on Jun. 5, 2018.

(51) Int. Cl.
| | |
|---|---|
| *B23K 26/36* | (2014.01) |
| *A61B 18/20* | (2006.01) |
| *B23K 26/14* | (2014.01) |
| *A61B 17/00* | (2006.01) |

(Continued)

(52) U.S. Cl.
CPC .......... *B23K 26/703* (2015.10); *A61B 18/20* (2013.01); *A61F 2/186* (2013.01); *B23K 26/36* (2013.01);
(Continued)

(58) Field of Classification Search
CPC ...... B23K 26/703; B23K 26/14; A61B 18/20; A61B 2017/00792; A61B 2018/00011;
(Continued)

(56) References Cited

U.S. PATENT DOCUMENTS

| | | |
|---|---|---|
| 7,101,365 B1 | 9/2006 | Sharon |
| 7,131,969 B1 | 11/2006 | Hovda et al. |

(Continued)

FOREIGN PATENT DOCUMENTS

| | | | | |
|---|---|---|---|---|
| CA | 2587331 A1 | * | 5/2006 | ......... A61B 18/1492 |

OTHER PUBLICATIONS

"BioOptics World Editors, Laser neurosurgery tool receives Health Canada license as Class 4 medical device, Oct. 6, 2014" (Year: 2014).*

(Continued)

*Primary Examiner* — Carl H Layno
*Assistant Examiner* — Aya Ziad Bakkar
(74) *Attorney, Agent, or Firm* — Shimokaji IP

(57) ABSTRACT

A device for shaping tissue includes a tip with an internal close-looped circulation system. The tip is configured to connect to tubes. One tube is configured to connect to a submersible cold-water pump. Another tube is an outlet. The tip has a sapphire window on one face and, on opposite face, a shaft with a laser fiber therein, and an opening for laser beam to shine through.

14 Claims, 5 Drawing Sheets

(51) Int. Cl.
*A61B 18/00* (2006.01)
*A61B 18/22* (2006.01)
*B23K 26/70* (2014.01)
*A61F 2/18* (2006.01)

(52) U.S. Cl.
CPC .............. *A61B 2017/00792* (2013.01); *A61B 2018/00011* (2013.01); *A61B 2018/00023* (2013.01); *A61B 2018/00327* (2013.01); *A61B 2018/00702* (2013.01); *A61B 2018/00791* (2013.01); *A61B 2018/2266* (2013.01); *B23K 26/14* (2013.01)

(58) Field of Classification Search
CPC ........... A61B 2018/00023; A61B 2018/00327; A61B 2018/00702; A61B 2018/00791; A61B 18/0218; A61B 2018/00642; A61F 2/186
See application file for complete search history.

(56) References Cited

U.S. PATENT DOCUMENTS

| | | | |
|---|---|---|---|
| 2006/0195073 A1* | 8/2006 | Connors | A61B 18/20 606/2 |
| 2016/0287334 A1* | 10/2016 | Grant | A61B 18/02 |
| 2017/0231651 A1 | 8/2017 | Dinger et al. | |
| 2021/0323232 A1 | 10/2021 | Schmale et al. | |

OTHER PUBLICATIONS

"Monteris Medical, NueroBlate Optic Laser Probes, 2018, Monteris Medical" (Year: 2018).*
Office action dated Jan. 1, 2021 in U.S. Appl. No. 16/432,318.
Office action dated Feb. 22, 2021 in U.S. Appl. No. 16/432,318.
Office action dated Apr. 5, 2021 in U.S. Appl. No. 16/432,318.
Office action dated Jun. 29, 2021 in U.S. Appl. No. 16/432,318.

* cited by examiner

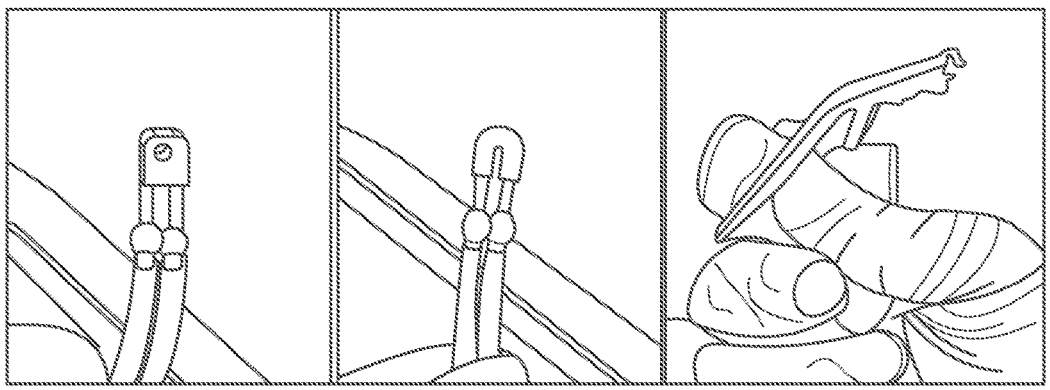
Figure 1: (left) Tip face with sapphire window. (middle) tip face with laser fiber shaft and hole, (right) previously flat piece of pig ear cartilage heated with laser into desired bent shape.
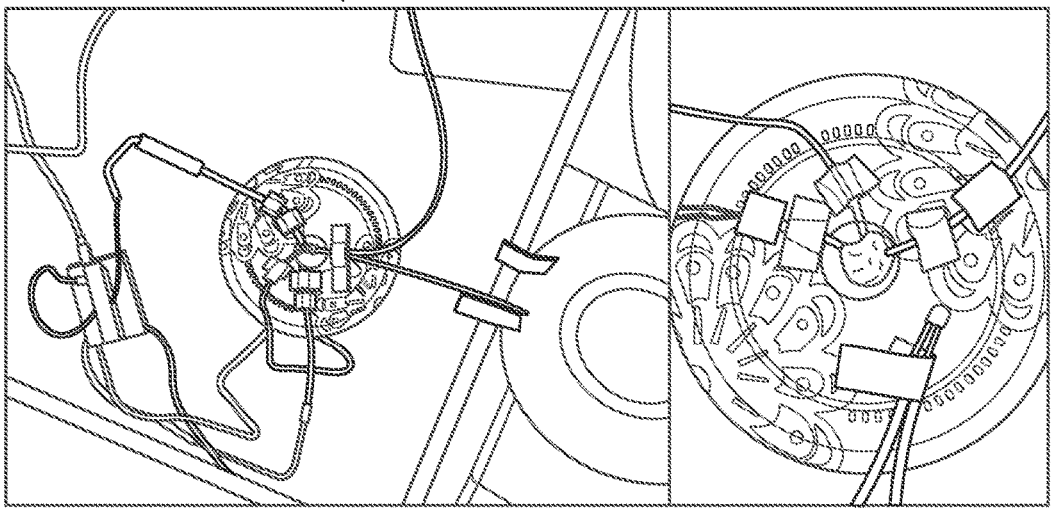
Figure 2: Cooling test with ballistic gel for temperature profile depth mapping.
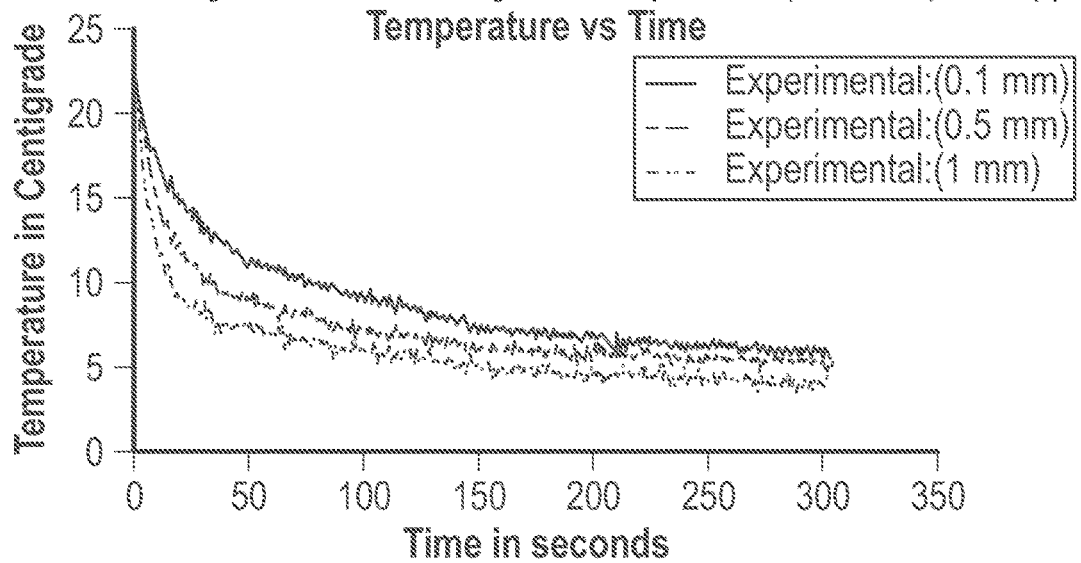
Figure 3: Tip cooled 10 degrees Celsius in 10 seconds.

Figure 4

| Trial # | Initial Temperature (C) | Next Steady State Temperature (C) | Time Elapsed (s) | Rate of Cooling (C/s) |
|---|---|---|---|---|
| 1 | 24.73 | 8.4 | 53 | 0.308 |
| 4 | 23.23 | 11.44 | 76.8 | 0.153 |
| 5 | 24.33 | 10.13 | 81.3 | 0.175 |
| 6 | 20.95 | 10.54 | 43.41 | 0.24 |
| 7 | 20.36 | 11.64 | 45.93 | 0.19 |
| 8 | 19.37 | 9.83 | 59.73 | 0.16 |
| 9 | 18.68 | 10.23 | 93.07 | 0.0908 |
| 11 | 10.03 | 7.48 | 102.9 | 0.0248 |
| 12 | 11.44 | 9.02 | 73.78 | 0.033 |
| 13 | 14.93 | 11.64 | 34.887 | 0.0943 |

DEVICE AND METHOD FOR THE PREPARATION AND OPERATION ON BIOLOGICAL SPECIMEN

CROSS REFERENCE TO RELATED APPLICATIONS

This application claims the benefit of and priority to U.S. provisional application No. 62/681,079, filed Jun. 5, 2018, which is incorporated herein by reference.

BACKGROUND OF THE INVENTION

The present invention generally relates to modification of tissue and, more particularly, to apparatus and methods of modifying cartilage.

Many people suffer from a nasal airway obstruction known as a deviated septum. A deviated septum is when the cartilage that separates the two nostrils is crooked, causing complications such as chronic sinus infections, nasal congestion, nose bleeds, difficulty breathing, and more.

The current solution to this problem is a surgical procedure called a septoplasty. This procedure is invasive, as the surgeon must cut through the layers of the nose in order to cut out the cartilage, cut it until it is straight, and then insert it back in. Oftentimes, the deviation is very severe and the surgeon must obtain cartilage from somewhere other than the septum in order to use to reshape it. It takes at least months in order for patients to know if the operation worked and to see if they feel a difference. It is common that patients do not notice improvement due to other complications that result from surgery, such as the formation of scar tissue, bone collapse, and excessive bleeding. Sometimes the procedure can cause infections, leading to long-term antibiotics.

As can be seen, there is a need for improved apparatus and methods of modifying the shape of tissue including cartilage.

SUMMARY OF THE INVENTION

In one aspect of the present invention, a device for shaping tissue, comprises a tip configured to connect to tubes; wherein one tube is configured to connect to a cold source; wherein another tube is configured as an outlet; wherein the tip has a window on one face and, on opposite face, a shaft with a laser fiber therein, and an opening for a laser beam to shine through.

In another aspect of the present invention, a device for shaping tissue comprises a tip having an internal closed-loop circulation system; a first tube and a second tube, both of which are connected to the internal closed-loop circulation system; wherein the first tube is connected to a cold source; wherein the second tube is connected to a discharge container; wherein the tip is configured to receive and convey a laser beam.

In a further aspect of the present invention, a system for shaping tissue comprises a computer; a laser source, in communication with the computer, and configured to generate a laser beam; a temperature sensor in communication with the computer; a tip in communication with the temperature sensor and configured to: receive and transmit the laser beam to the tissue; and transfer heat from the tip to a cooling fluid inside the tip.

In an additional aspect of the present invention, a method of shaping tissue comprises directing a laser beam at the tissue; monitoring temperature at a location on or near the tissue; modulating the laser beam according to the monitored temperature; cooling the location on or near the tissue; and modulating a rate of the cooling.

In yet another aspect of the present invention, a non-transitory computer readable medium with computer executable instructions stored thereon, executed by a processor, to perform a method of shaping tissue, the method comprises focusing a laser beam at the tissue; monitoring temperature at a device on or near the tissue; modulating the laser beam according to the monitored temperature; cooling the device; and modulating a rate of the cooling.

These and other features, aspects and advantages of the present invention will become better understood with reference to the following drawings, description and claims.

BRIEF DESCRIPTION OF THE DRAWINGS

FIG. 1 are pictures of a device and modified cartilage according to embodiments of the present invention;

FIG. 2 are pictures of a system according to an embodiment of the present invention;

FIG. 3 is a graph of temperature versus time according to an embodiment of the present invention;

FIG. 4 is a table of test results according to embodiments of the present invention;

DETAILED DESCRIPTION OF THE INVENTION

Figure 5:
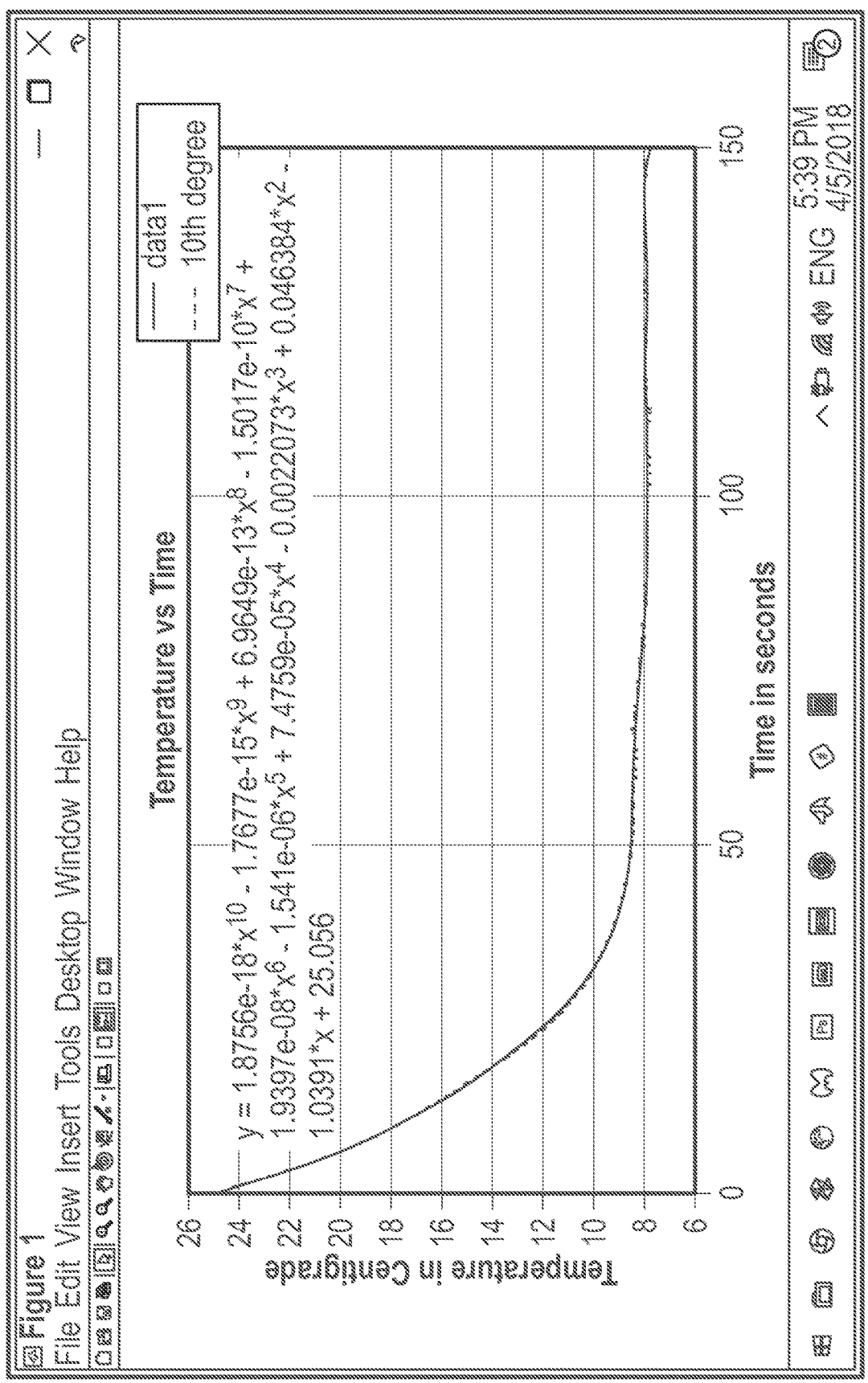
FIG. 5 is a graph of temperature versus time according to another embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, the present invention provides a medical device and method that can heat, cool, prepare, manipulate, and operate on cells, tissue, bone, and biological specimens. It can use a laser spectrum of 500-11000 nm on cells, tissue, bone, and biological specimens allowing it to be heated, cooled, vaporized, stimulated, shaped, activated, and ablated.

The medical device according to the present invention can prepare and operate on biological specimens without damaging surrounding cells, tissue, bone, or the biological specimen. It can include a 7 mm metal tip designed with an internal closed-looped circulation system. The tip can be connected to tubes in which one end connects to a submersible cold-water pump, and the other tube is the outlet. Iced saline solution can be pumped into the tip allowing it to drastically cool to 0 degrees Celsius. The tip can have a 2 mm sapphire window, or plate, on one face, which also cools along with the metal. On the opposite face, there can be a shaft to fit a laser fiber and an opening for a laser beam to shine through. The sapphire window can have optical properties for high transmission of laser wavelengths. The device can irradiate pulsed laser beams with continuous contact cooling in order to heat the deeper tissue while avoiding thermal injury to the surface tissue.

This present invention allows for a safer and less invasive route than traditional septoplasty, or other procedures that require excision for in-vivo preparation and operation of biological specimen. Patients can notice results within one or two days, as opposed to months to years. The patient does not have to undergo anesthesia or surgery. The present invention can make septoplasties more efficient and faster. Surgeons can perform procedures with the inventive device at the point-of-care.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable media having computer readable program code embodied thereon.

Any combination of one or more computer readable storage media may be utilized. A computer readable storage medium is an electronic, magnetic, optical, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium is any tangible medium that can store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable storage medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
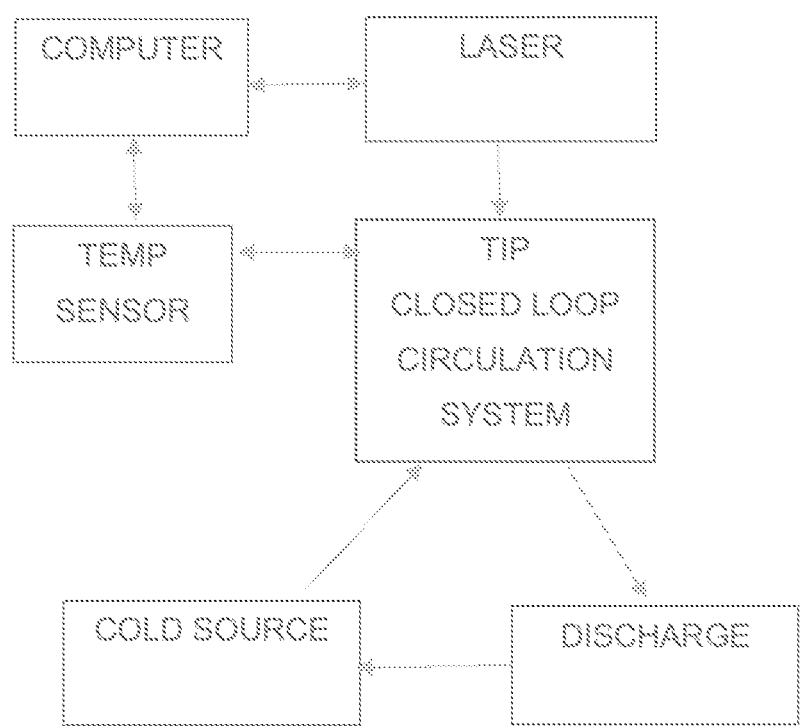
FIG. 6 is a schematic diagram of a system according to an embodiment of the present invention.

FIG. 6 schematically depicts a system according to an embodiment of the present invention. The system may include a laser source in communication with a tip having a closed-loop circulation system. A temperature sensor can sense temperature of the tip. A computer having a database and processor can control the laser output based on temperature signals from the sensor. The tip, and more specifically one end of the closed-loop circulation system, can receive a cooling fluid or medium from a cold source. The cooling fluid can be discharged from the tip, and more specifically from another end of the closed-loop circulation system, to a discharge container for circulation back to the cold source.

Accordingly, it can be appreciated that the present invention also provides a method and non-transitory computer readable medium with computer executable instructions stored thereon to perform shaping of tissue.

One or either of the foregoing can include one or more of the steps of directing a laser beam at the tissue; monitoring temperature at a location on or near the tissue; modulating the laser beam according to the monitored temperature; cooling the location on or near the tissue; and modulating a rate of the cooling. Directing the laser beam can include passing the laser beam through a sapphire window of, for example, a metal tip that is on or near the tissue. Modulating the laser beam can include changing an intensity of the laser beam. Cooling can include moving a cooling fluid near the tissue, such as through a tip on or near the tissue, as well as modulating a rate of flow of the cooling fluid.

One or either of the method and medium can include one or more of the steps of focusing a laser beam at the tissue; monitoring temperature at a device on or near the tissue; and cooling the device. Focusing the laser beam can include directing the laser beam through a window of the device which can be a metal tip. Cooling can include moving a cooling fluid through the device.

Figure 7:
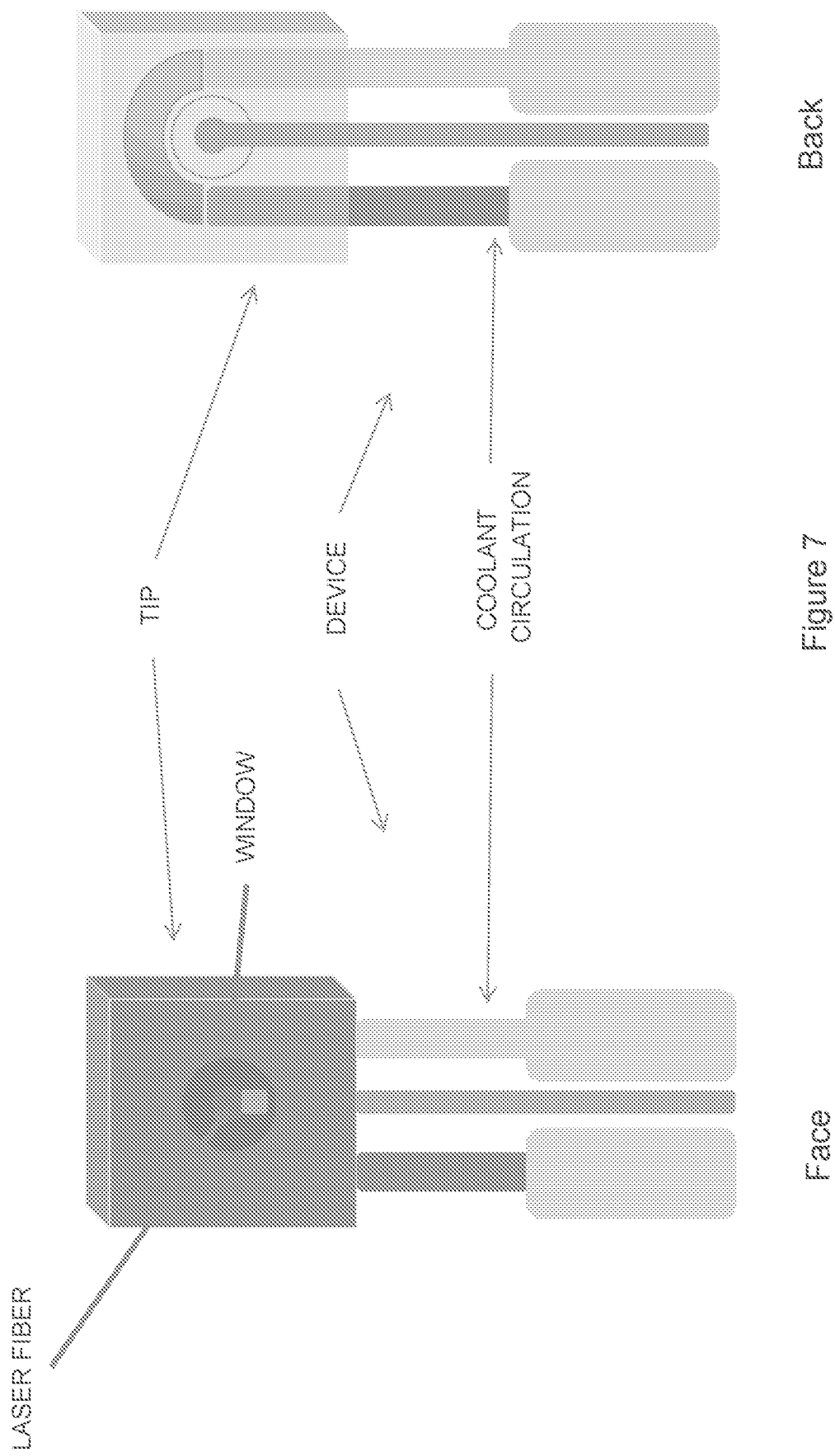
FIG. 7 is a plan view of the device shown in the left and middle pictures of FIG. 1.

FIG. 1 depicts: (left) is a tip face with sapphire window, (middle) tip face with laser fiber shaft and hold, and (right) previously flat piece of pig ear cartilage heated with laser into desired bent shape. FIG. 7 is a plan view of the left and middle pictures in FIG. 1.

FIG. 2 is a cooling test with ballistic gel for temperature profile depth mapping.

FIG. 3 is a tip cooled 10 degrees Celsius in 10 seconds.

Prototype Device Test Protocol

Purpose

The below outlines the testing procedures to test the cooling capabilities of the prototypes developed, particularly with how quick the device is able to drop in temperature.

Scope

The scope of the protocol is limited to testing and proving the cooling functionality of all prototypes manufactured.

Background

We are developing multiple prototype devices that will provide active cooling to the mucous membrane of the nasal cavities during laser treatment of the nasal septum. This test protocol is for the purpose of testing proof of concept for the theory as well as proving functionality of the device. This particular protocol will be devoted to testing the cooling capabilities of the prototype.

EQUIPMENT AND MATERIALS

Large container
Prototype device
Submersible pump
2 mm diameter clear plastic tubing
Water resistant epoxy
Thermally conductive adhesive
Cold temperature fluid
Thermistor
Arduino
Procedure
  Assemble tubing system to be fitted with the prototype.
  Fit the tubing from the submersible pump to the device inlet and set up tubing for the outlet.
  Use the thermal adhesive to attach the thermistor where the sapphire window sits in the prototype. (If this has already been done, skip this step).
  Set up the submersible pump inside aforementioned container; do NOT plug it in yet.
  Fill a large container with a cold temperature fluid.
  Examples include: cold water, cold saline water, water with ice dumped inside.
  Setup the thermistor with an Arduino (code is provided on Drive).

The code will measure temperature (C) versus time (milliseconds).
  Start the Arduino's serial monitor.
  Let the prototype sit at room temperature until steady state.
  Turn on the pump.
  Record data from Arduino serial monitor and use MATLAB to interpret data (code is also provided on Drive).
Acceptance Criteria
  Ideally, the lower the temperature, the better. Specifically, a 10C drop in temperature would satisfy the proof of concept.

FIG. 4 is a table of test results. Steady state is defined as having a constant temperature for the duration of 5 seconds. Rate of cooling is calculated as a linear quantity; however, the data reflects behavior of exponential decay (i.e., a lower temperature can be expected). Trial 1 had the best results (higher saline concentration).

The equation fitting this curve (FIG. 5) of trial 1 is:

$$y=(1.8756E-18)*(x^{10})-(1.7677E-15)*(x^9)+ \\ (6.9649E-13)*(x^8)-(1.5017E-10)*(x^7)+ \\ (1.9397E-8)*(x^6)-(1.541E-6)*(x^5)+ \\ (7.4759E-5)*(x^4)-(0.0022073*x^3)+ \\ (0.046384*x^2)-(1.0391*x)+(25.056)$$

The way the tubing was attached to the device was unsatisfactory. Leaks were present, as the tubing was not sealed sufficiently. Using epoxy/JB Weld would help to mitigate this problem, but this becomes a more permanent method in attaching the tubing and the device. With the limitations of 3D printing in metal, a proper valve is not able to be manufactured. More options will be explored, in making the attachment of the tubing, to accomplish a removable and leak-proof design The elevation at which the pump is placed absolutely matters. Gravity plays a large role, and as the pump is placed higher, a higher flow rate is achieved. Higher flow rates enable us to reach lower temperatures depending on the source of cold temperature fluid the pump is using. This scenario is best seen on trial #11.

As we conduct more trials using saline and ice, the concentration of saline goes down because more ice needs to be added as testing goes along. This ultimately raises the freezing point marginally. A possible solution to this is to surround the container of saline with another container filled with a cryogen, seeing as an infinite source of saline is not an option.

Laser Testing
  1530 nm and 1438 nm wavelength laser
    1530 nm wavelength
      maxed out at 65 degrees C.
      12 amps
    1438 nm wavelength
      Reached 85 degrees C. and higher after 20 seconds
      12 amps
      Used to test if could deform cartilage
      Tested laser on raw chicken to visual heating
      Deepest level of cooking around 2 mm with 1438 nm for 5 minute holds
      Tested cartilage from pig ear and deformed it
Results
  Laser significantly bent previously straight piece of pig ear cartilage, without visible damage to mucosa.
  Cooling and laser will be tested together to map out temperature profile and validate theoretical model.

It should be understood, of course, that the foregoing relates to exemplary embodiments of the invention and that modifications may be made without departing from the spirit and scope of the invention as set forth in the following claims.

We claim:

1. A device for shaping tissue, comprising:
a tip configured to connect to tubes;
wherein one tube is configured to receive a cooling fluid from a cold source;
wherein another tube is configured as an outlet for the cooling fluid;
wherein the tip has a window in one exterior planar face thereof and, on opposite exterior planar face thereof, a shaft with a laser fiber therein, and an opening in the opposite exterior planar face for a laser beam from the laser fiber to shine through;
wherein the tip is made of a laser non-transmissive material;
wherein the window is made of a laser transmissive material.

2. The device of claim 1, wherein the tip is made of metal.

3. The device of claim 1, wherein the tip is configured with an internal close-looped circulation system.

4. The device of claim 1, wherein the cold source includes a cold-water pump.

5. The device of claim 1, wherein the cold source includes an iced saline solution.

6. The device of claim 1, wherein the window is a sapphire window.

7. The device of claim 1, wherein the tip is configured to cool to 0° C.

8. A system for shaping tissue, comprising:
a computer;
a laser source, in communication with the computer, and configured to generate a laser beam;
a temperature sensor in communication with the computer;
a tip in communication with the temperature sensor and configured to:
receive and transmit the laser beam to the tissue; and
transfer heat from the tip to a cooling fluid inside the tip;
wherein the tip has a window in one exterior planar face thereof and, on opposite exterior planar face thereof, a shaft with a laser fiber therein, and an opening in the opposite exterior planar face for a laser beam from the laser fiber to shine through;
wherein the tip is made of a laser non-transmissive material;
wherein the window is made of a laser transmissive material.

9. The system of claim 8, wherein the computer is configured to modulate the laser beam.

10. The system of claim 9, wherein the computer modulates the laser beam in response to temperature signals from the temperature sensor.

11. The system of claim 8, wherein the window is made of sapphire.

12. The system of claim 8, wherein the tip includes a closed-loop circulation system that hold the cooling fluid.

13. The system of claim 8, further comprising a cold source in communication with the tip.

14. The system of claim 8, further comprising a discharge container in communication with the tip.

* * * * *